(12) United States Patent
Venturini et al.

(10) Patent No.: US 11,006,987 B2
(45) Date of Patent: May 18, 2021

(54) INTERNAL PLATE FIXATION DEVICE

(71) Applicant: ORTHOFIX S.R.L., Bussolengo (IT)

(72) Inventors: Daniele Venturini, Bussolengo (IT); Marco Magni, Ferrara (IT); Andrea Zaccaria, Tregnago (IT)

(73) Assignee: ORTHOFIX S.R.L., Bussolengo (IT)

( * ) Notice: Subject to any disclaimer, the term of this patent is extended or adjusted under 35 U.S.C. 154(b) by 271 days.

(21) Appl. No.: 16/303,869

(22) PCT Filed: May 24, 2017

(86) PCT No.: PCT/EP2017/062653
§ 371 (c)(1),
(2) Date: Nov. 21, 2018

(87) PCT Pub. No.: WO2017/215896
PCT Pub. Date: Dec. 21, 2017

(65) Prior Publication Data
US 2020/0323569 A1 Oct. 15, 2020

(30) Foreign Application Priority Data
Jun. 17, 2016 (EP) ..................................... 16425059

(51) Int. Cl.
*A61B 17/80* (2006.01)
*A61B 17/86* (2006.01)
(52) U.S. Cl.
CPC ...... *A61B 17/8052* (2013.01); *A61B 17/8635* (2013.01)
(58) Field of Classification Search
CPC combination set(s) only.
See application file for complete search history.

(56) References Cited

U.S. PATENT DOCUMENTS 8,273,111 B2 9/2012 Amato et al.
2004/0111089 A1* 6/2004 Stevens .............. A61B 17/1728
606/86 B (Continued)

FOREIGN PATENT DOCUMENTS

EP 2 364 658 A1 9/2011

OTHER PUBLICATIONS

International Preliminary Examning Authority, "Search Report" in application No. PCT/EP2017/062653, dated Aug. 24, 2018, 16 pages.

(Continued)

*Primary Examiner* — Sameh R Boles
(74) *Attorney, Agent, or Firm* — Hickman Becker Bingham Ledesma LLP; Malgorzata A. Kulczycka

(57) ABSTRACT

The present invention relates to an internal bone plate fixation device (1) for use as a means of synthesis in anatomical regions or epiphysis/metaphysis with poor coating of soft tissues, of the type comprising a bone plate (2) that is bilobate or having eight-like shape, comprising a pair of portions (23, 24) adapted to be respectively associated to the epiphysis and to the metaphysis of a bone and joined by a central portion (15) and in each of which is formed at least one through hole (3, 4) to receive a corresponding screw (5) for fixing to the bone. Advantageously, the bone plate (2) is flat with almost constant thickness and is delimited by opposite surfaces (6, 7) parallel with a single recess (8) or notch that is transversal to the longitudinal axis of bone plate (2) formed on only one (6) of said surfaces (6, 7), with the thickness (s) of the plate being less than a ninth of its maximum longitudinal extension (L).

14 Claims, 7 Drawing Sheets

(56) References Cited

U.S. PATENT DOCUMENTS

| | | |
|---|---|---|
| 2013/0325073 A1 | 12/2013 | Sikora et al. |
| 2014/0005729 A1 | 1/2014 | Dimatteo |
| 2014/0277176 A1 | 9/2014 | Buchannan et al. |
| 2015/0223852 A1* | 8/2015 | Lietz ................ A61B 17/8057 606/289 |
| 2018/0021050 A1* | 1/2018 | Little ................ A61B 17/8085 606/280 |

OTHER PUBLICATIONS

European Patent Office, "Search Report" in application No. PCT/EP2017/062653, dated Sep. 15, 2017, 4 pages.

* cited by examiner

INTERNAL PLATE FIXATION DEVICE

FIELD OF THE INVENTION

The present invention relates to an internal plate fixation device for use as a means of synthesis in anatomical regions with poor coating of soft tissues, of the type comprising a bone plate wherein at least a pair of through holes are provided to receive screws for fixing to the bone.

The invention relates in particular, but not exclusively, to an internal plate fixation device intended to improve the tolerability for the patient of the treatment of fracture synthesis or the treatment of bone deformations and that provides for the application of such plate under the skin, in the epiphysis of anatomical regions which are poorly covered by soft tissues.

The invention may be usefully applied in the field of pediatric orthopaedics, for example for epiphysiodesis interventions at the ends of deformed long bones of paediatric patients and the following description is made with non-limiting intent to the use in the context of this sector.

In the specific field of the present invention, some problems are known which are due to poor tolerability of bone fixation plates in certain anatomic regions, including the knee, elbow and backbone, which do not have substantial thicknesses of soft tissues.

For example, the use of these plates on the epiphysis located close to the articulations sometimes causes local inflammation due to the projection from the plates of the heads of the screws for fixing to the bone.

The bone plate is positioned by means of fixing screws, which fasten it respectively to the epiphysis and metaphysis at the convex area of bone deformation. Both the metaphyseal and epiphyseal portions of the plate in fact have at least one through hole which is suitable for accommodating said fixing screw.

There are known in the prior art particular eight-like shaped plates which are fixed to the bone by means of fixing screws which may diverge to avoid compression of growth cartilage and carefully guide the natural process of growth of the physis and bones, without the need for a more invasive osteotomy intervention.

The fixing screws are loosely constrained inside the respective holes, so as to be able to vary their angle, gradually adapting to the process of bone growth. In fact, during the growth of physial tissue, the fixing screws are subjected to a dragging action which determines a progressive angular spreading, i.e. the two screws are tilted outwardly with respect to the median plane passing through the physis.

PRIOR ART

A solution currently adopted in the prior art is described in U.S. Pat. No. 8,273,111, which relates to a plate fixation device for the control of bone development, in particular for correcting bone deformities. This device may comprise a bone plate having a stepped profile defined by a first level, a second level and an intermediate ramp that connects them, wherein in each level there is a threaded hole for receiving a screw for fixing to the bone.

Also described is a variant of this plate, characterised by an intermediate portion in the shape of an arch or bump, used depending on the anatomical contour of the specific patient or on the bone. In this way one avoids overloading the physis of the bone or injuring it during the period of correction, for example when it is to be implanted in a patient of paediatric age to correct a growth that is non-symmetrical or an anatomic deformity.

In order to improve the tolerability of these plates in anatomical regions with poor coating of soft tissues, a solution is used that can be defined as "integrated washer", which locally increases the thickness of the plate toward the bone at the through holes for the fixing screws. In this way the protrusion of the head of the screws can be reduced with respect to the upper profile of the plate, but only during the implantation step.

Another solution adopted by the prior art is described in US patent application US 2004/0111089, which relates to an implant to realign the angular and rotational deformations of long bones in patients with active bone growth.

Such implant for bone alignment comprises a guide wire, a plate and two bone mountings. In particular, by means of the guide wire the growth cartilage is identified while the bone fixings are placed in the bone through the holes of the plate, connecting the sections of the bone on opposite sides of the physis with the implant. The implant is designed in such a way as to partially limit the volume of bone growth on the side of the physis in which it is placed, that is, promoting growth on the physis of new bone tissue in such a way that the direction of growth and the resulting alignment are achieved in a controlled manner.

Although the implants known in the prior art partly solve the technical problem shown above, they do however have some limitations, for example the excessive protuberance of the heads of the screws which fix the plate to the bone, making bothersome and less tolerable such plates in anatomical regions which are essentially lacking of soft tissue.

In this content it is not possible to adopt structures like the one disclosed in the US patent application No. US 2014/0005729 that may not be considered a eight-like shaped plate and is specifically related to a tissue repair suture plate. Such a plate is not suitable for treating bone fractures and present a weakening or cut portion 36 for being bent during the implantation into a recessed portion of a bone.

Another solution is disclosed in the US patent application No. US 2015/223852 relating to an elongated bone plate including a plurality of threaded passing holes for hosting threaded heads of bone screws. This plate is adapted for fractures of long bones e certainly not for epiphysiodesis interventions.

Furthermore, the plate configurations adopted in the prior art to prevent the crushing of the growth cartilage can sometimes affect the strength of the plate itself and make it relatively fragile.

The technical problem underlying the present invention is to devise a means of synthesis, composed of a plate and screws, for improving the tolerability of such device when applied in anatomical regions with poor coating of soft tissues and characterised by such structural and functional properties so as to avoid the lateral compression of the growth cartilage.

Another object of the invention is to provide a fixation device with a simple and economical structure that guarantees also a certain strength for the whole duration of its implantation stage.

A further object of the invention is to make more tolerable to the patient the possible projection of the heads of the bone fixing screws even when the corresponding plate is located in the epiphysis covered by poor muscle layers or soft tissues.

SUMMARY OF THE INVENTION

The present invention relates to an internal bone plate fixation device as claimed in the annexed claims. Preferred embodiments are set forth in the dependent claims.

The solution idea underlying the present invention is to provide a plate of a suitable thickness for epiphysiodesis interventions allowing an increase of the sinking of the head of the screw in a cup-like shaped or hemispherical housing seat formed in the plate itself, leaving substantially unchanged the flexibility of the plate forming a transversal notch, centrally located, capable of housing the growth cartilage.

On the basis of this solution idea, the technical problem is solved by an internal bone plate fixation device for use as a means of synthesis in anatomical regions or epiphysis with poor coating of soft tissues, of the type comprising a bone plate which is bilobate or having eight-like shape comprising a pair of portions adapted to be respectively associated to the epiphysis and to the metaphysis and which are joined by a restricted central portion; in each of said portions being formed at least one through hole for receiving a corresponding screw for fixing to the bone, characterised in that the bone plate is flat with almost constant thickness and is delimited by opposite parallel surfaces with a single recess or notch which is transversal to the longitudinal axis of the bone plate formed on only one of said surfaces; the thickness of the plate being less than an eighth of its maximum longitudinal extension.

Essentially, this thickness is chosen in a range between 1.5 and 2.3 mm.

More in particular, said thickness is chosen equal to 2.1 mm, with a machining tolerance of at least 5%.

It should also be noted that the notch is arched and is formed in the central portion of joining; the thickness of the plate at this notch is selected in a range between 1.3 and 1.7 mm.

More in particular, the thickness corresponding to said notch is chosen equal to 1.5 mm, always with a machining tolerance of at least 5%.

It is understood that all the measures mentioned above have a machining tolerance of at least 5%.

The bone plate of the present invention is bilobate and having substantially an eight-like shape.

The plate includes at least a third through hole in the central portion of joining for receiving a guiding cable for temporary fixing.

Furthermore, each of the holes of the lobed portions of the plate has, on the surface opposite to said notch, a circular mouth that provides access to a cup-like shaped or hemispherical seat for the tilting housing of the head of a corresponding fixing screw.

A cylindrical hole opened onto the bottom of said cup-like shaped seat is also intended to accommodate the stem of a corresponding fixing screw while at least one groove, tapered both onto the cup-like shaped seat and in the cylindrical hole, is provided in a bottom portion of the cup-like shaped seat toward the extremity of the plate.

This groove can be obtained by means of a hole of a cylindrical or conical shape having an axis which is tilted with respect to the axis of said cylindrical hole.

The features and advantages of the internal plate fixation device of the present invention, will become apparent from the description of an embodiment, provided as an illustrative and non-limiting example with reference to the accompanying drawings.

DETAILED DESCRIPTION OF PREFERRED EMBODIMENTS

Figure 1:
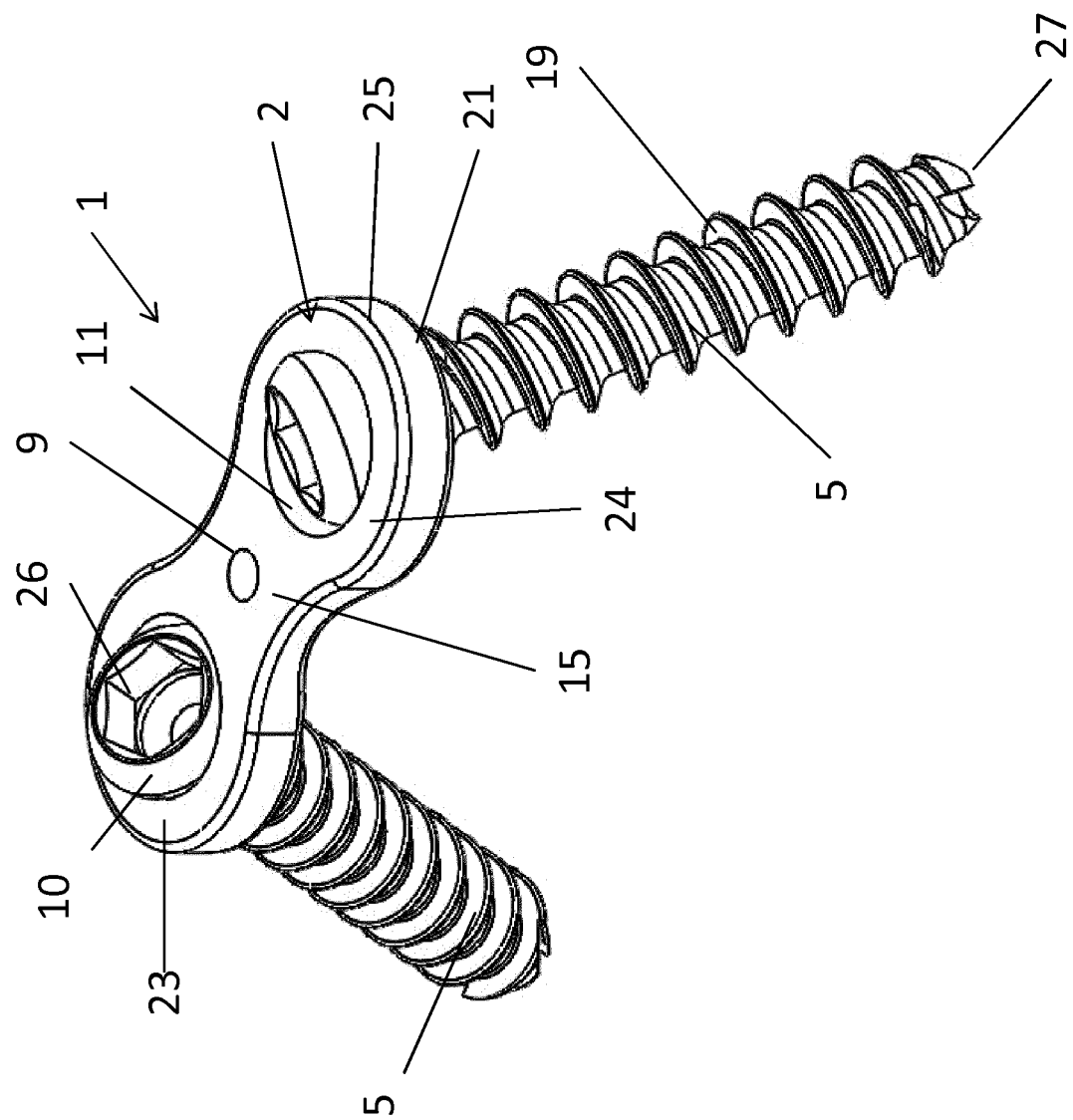
FIG. 1 shows a schematic perspective view of an internal bone plate fixation device made in accordance with the present invention.
Figure 2:
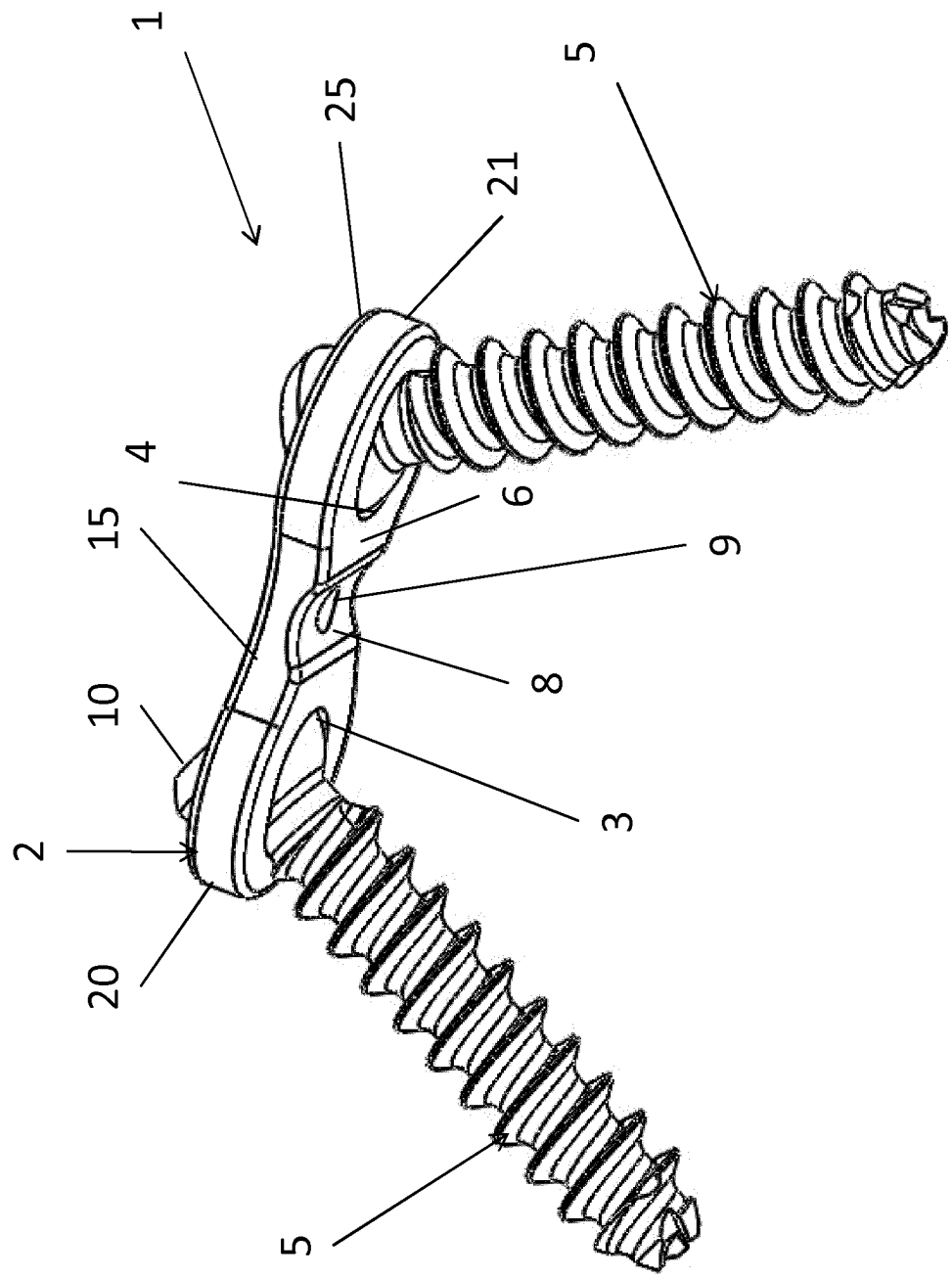
FIG. 2 shows a schematic perspective view of the fixation device of FIG. 1 from a different point of view.
Figure 3:
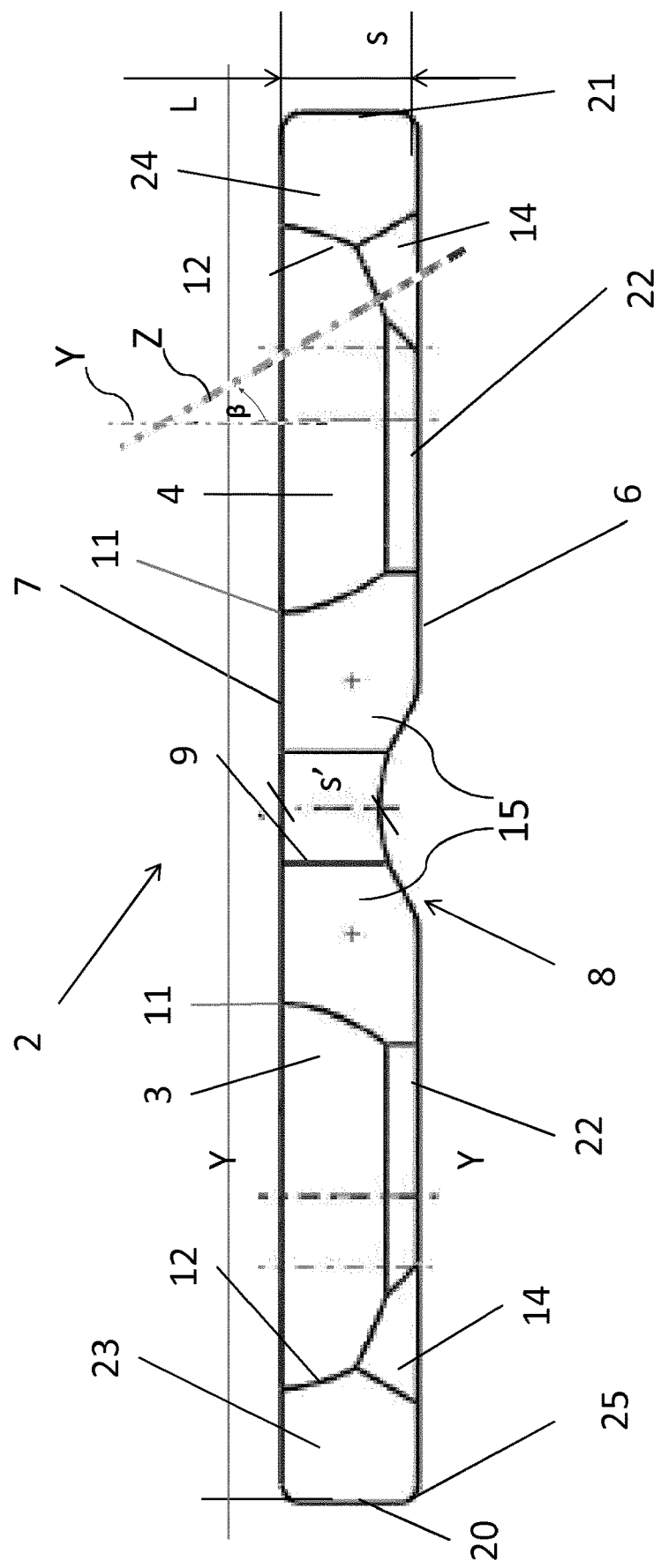
FIG. 3 shows a side sectional view of a bone plate of the device of FIG. 1.
Figure 4:
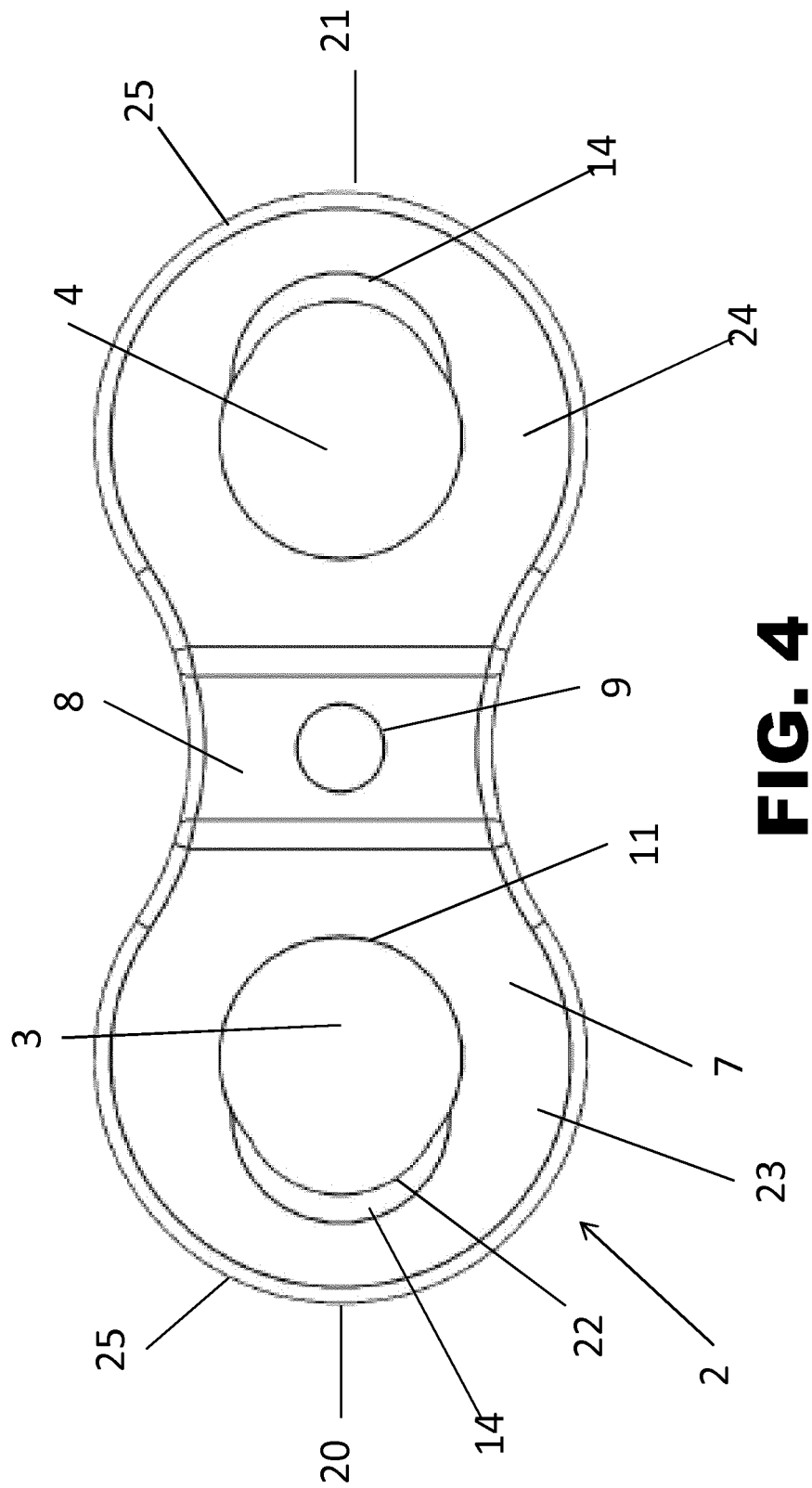
FIG. 4 shows a bottom view of the plate shown in FIG. 3.
Figure 5:
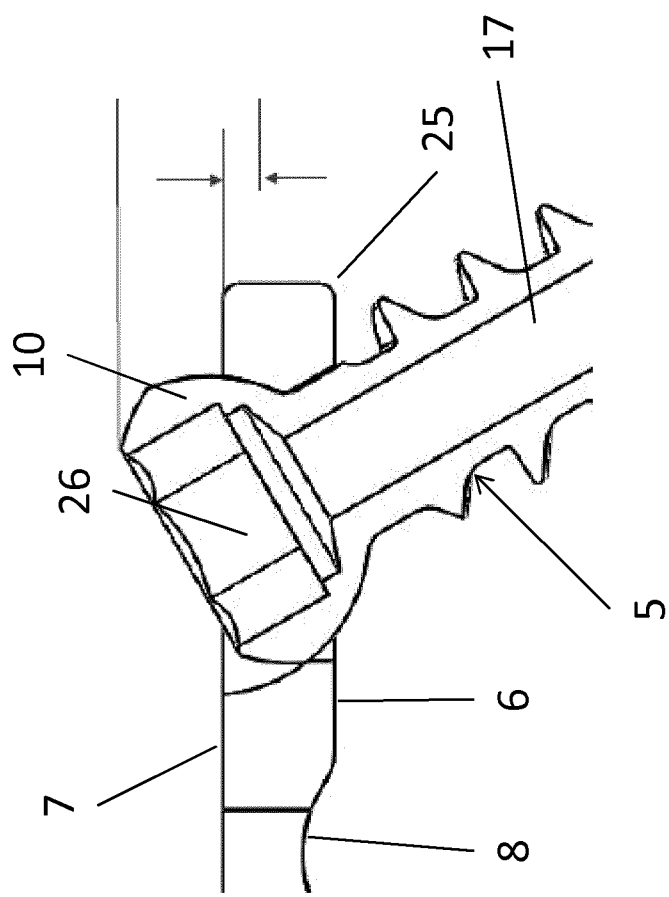
FIG. 5 shows a partial side view of a detail of the fixation device according to the invention.

With reference to these figures, and in particular to the example of FIG. 1, reference 1 globally and schematically indicates the internal fixation device for bone plate 2, improving the tolerability of such plate in anatomical regions with low or moderate covering of soft tissues.

The fixation device 1 of the present invention is particularly, although not exclusively, suitable for use in orthopaedics for the resolution of bone fractures of bone fragments or for the care of malformations of long bones in patients of a paediatric and/or adolescent age, by application of the fixation device over the physis of these bones.

Such bone plate 2 is preferably made of a rigid and biocompatible material (for example titanium) and has bilobate eight-like shape, of uniform thickness, developing over a longitudinal direction which is more prominent than the transversal direction.

The bone plate 1 is flat with almost constant thickness and presents two opposite parallel surfaces, 6 and 7, the first of which is configured to be put in contact with the bone surface. For sake of simplicity, in the continuation of this description we will describe the first surface as bottom surface 6 and the second surface opposite thereto as top surface 7 of the bone plate 2. Any positional references used in the present description and comprising indications such as lower or higher, below or above, or similar expressions, will always be referred to the orientation of the aforementioned surfaces.

The bone plate 2 having eight-like shape comprises a first portion 23 and a second portion 24 adapted to be respectively associated to the epiphysis and to the metaphysis of a long bone of a patient of paediatric age, for example a bone showing an angular deformation to be corrected with the application of fixation device 1 of the present invention.

The two portions of the eight-like shape are interconnected by means of a joining central portion 15, which provides a sole localised restriction or tapered portion of the bone plate 2. This portion of joining 15 has a guiding through hole 9 adapted to facilitate the first implantation of the bone plate 2 by means of a guiding wire (not shown) in such a way that the connecting portion 15 is arranged over the physis in growth, in between the epiphysis and metaphysis.

The bone plate 2 has symmetrical shape with respect to a transversal plane passing through the centre of the fitting portion 15.

The areas belonging to the first portion 23 and to the second portion 24, placed at the maximum distance from the transversal plane passing through the centre of portion 15 of joining, respectively define first extremity 20 and second extremity 21 of the bone plate 2.

The first portion 23 is crossed by a first through hole 3 adapted to receive a fixing screw 5.

Furthermore, the second portion 24 is crossed by second through hole 4 adapted to receive a corresponding fixing screw 5.

The bone plate 2 has peripheral edges 25 of the two lower and upper surfaces 6 and 7 which are rounded.

Figure 6:
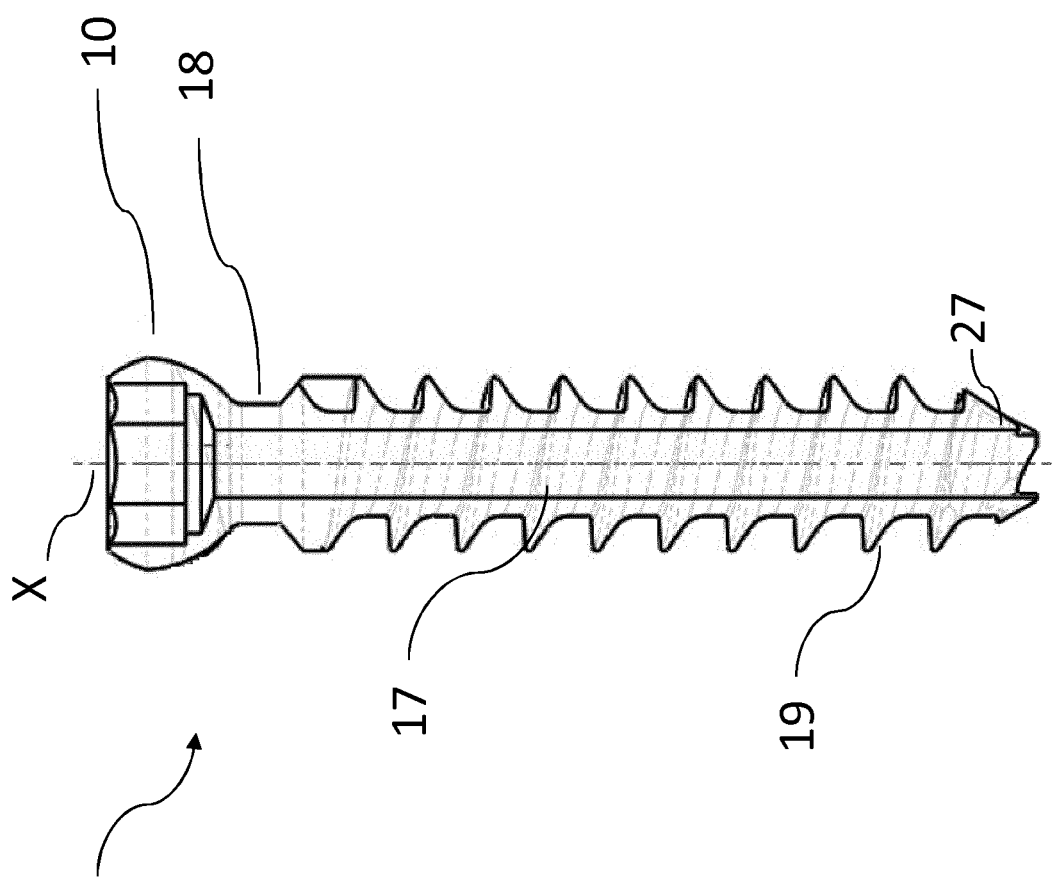
FIG. 6 shows a side sectional view of the screw for fixing the fixation device of FIG. 1.
Figure 7:
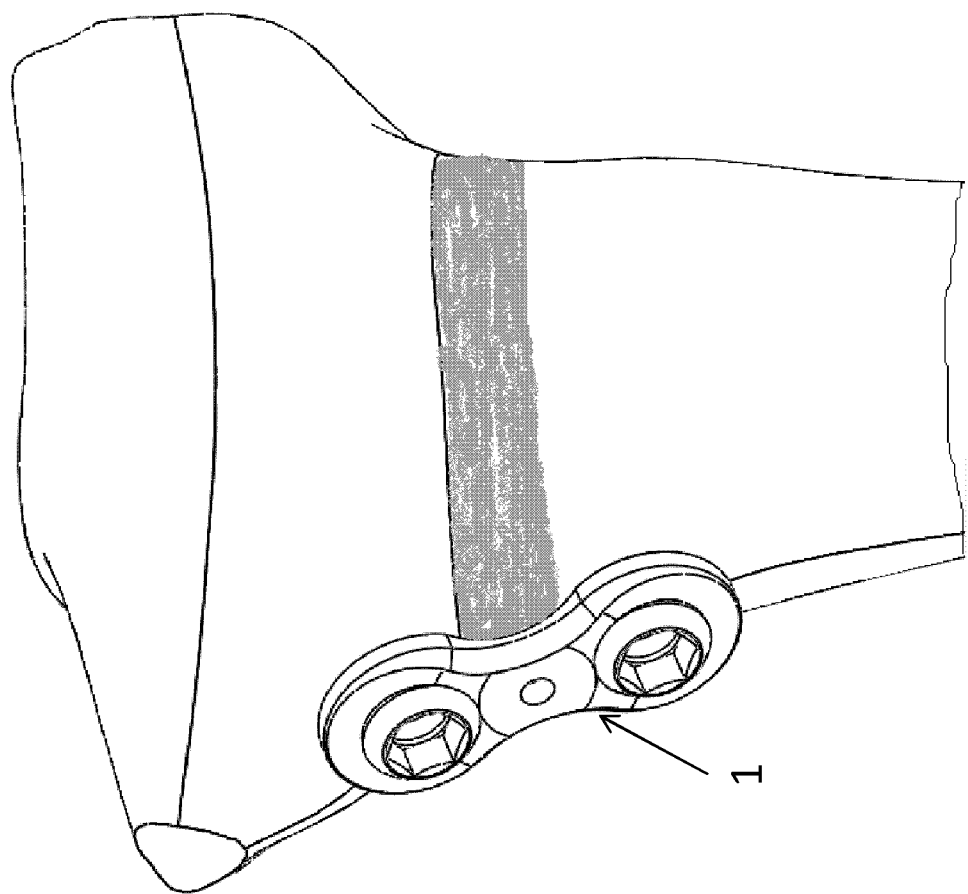
FIG. 7 shows a schematic perspective view of the internal fixation device according to the invention, in use.

In a preferred embodiment, the fixing screw 5, visible in its entirety in FIG. 6, comprises a head 10, which is preferably spherical, placed at the end of a stem directed according to a longitudinal axis X. The stem has a non-threaded portion 18 close to the head, a further threaded portion 19, preferably having a thread with triangular profile, and finally a self-threading tip 27 opposite to the head 10. The stem is crossed by an internal guiding cannula 17 that opens onto a hexagonal cavity 26 inside the head 10.

By virtue of the aforementioned symmetry of the bone plate 2, the through hole 3 of the first portion 23 and the through hole 4 of the second portion 24 are equal and opposite. For the sake of simplicity, the internal conformation of only one of the holes 3, 4 will be further described, such description applying for symmetry to both holes;

similarly, the same reference numbers will be used for the same symmetrical conformations of holes 3,4.

The hole 4 comprises a cup-like shaped seat 12, preferably hemispherical, for the tilting housing of the head 10 of the fixing screw 5.

The cylindrical hole 22, which opens onto the bottom of said cup-like shaped seat 12, is meant to accommodate the stem 18 of said fixing screw 5.

At least one groove 14 tapered onto the cup-like shaped seat 12 and in the cylindrical hole 22 is provided on a bottom portion of the cup-like shaped seat 12 toward the extremity 21 of the plate 2, towards the lower surface 6.

The cup-like shaped seat 12 defines a spherical coupling with the head 10 housed therein, allowing complete freedom of movement to the stem 18 of the screw 5. In particular, the fixing screw 5 will thus be able to tilt in a plane longitudinal to bone plate 2, in a direction away from the median plane passing through the physis, until reaching a point of abutment or end.

The cup-like shaped seat 12 comprises in particular an input section 11, preferably circular, adapted to allow the insertion of the head 10 of the fixing screw 5 in the hole 4 and outlet section 22 of a size at least locally reduced with respect to the section of the inlet section 11 to allow holding of the head 10 of the fixing screw 5 inside the cup-like shaped seat 12.

As mentioned above, the cup-like shaped seat 12 is preferably of a hemispherical shape, with axis Y orthogonal to the bone plate 2 and passing substantially through the centre of the inlet section 11.

The cylindrical hole 22 develops coaxially to the cup-like shaped seat 12, and has a diameter equal to that of the outlet section.

The groove 14 tapers into the cup-like shaped seat 12 thus determining a lower enlargement of the outlet section while moving away from the central portion 15 of joining.

The groove 14 may be provided for example by a cylindrical, or conical, tilted hole, tapered onto the cup-like shaped seat 12. Such groove 14 being a hole of cylindrical or conical shape can have a major diameter of greater size than, or even equal to, the diameter of the non-threaded upper portion 18 of the stem of the fixing screw 5 and having an axis Z tilted of an angle β with respect to the axis Y of the through hole 4. The hole 14 opens onto the outer lateral periphery of the cup-like shaped seat 12 and extends downwards and toward the outside, i.e. toward a respective extremity 20 or 21 until it reaches the lower surface 6 of the plate. The hole 14 remains in communication with the cylindrical hole 22 along its entire extension.

This tilted cylindrical holed groove 14 is provided by material machining from the area surrounding the cup-like shaped seat 12 at extremities 20, 21, by means of a drilling operation.

Advantageously, according to the invention, the bone plate 2 has a thickness "s" that is sturdy with respect to the solutions of the prior art.

More in particular, thickness "s" of the plate 2 is less than an eighth of its maximum longitudinal extension L, from extremity 20 to extremity 21. Thickness "s" refers to the thickness of the two uniform portions 23 and 24.

Thickness "s" can be chosen in a range between one eighth and one twelfth of the maximum longitudinal extension L.

In a preferred embodiment, such thickness "s" can be chosen in a range between 1.5 and 2.3 mm, with a machining tolerance of at least 5%.

More in particular, the thickness "s" is chosen equal to 2.1 mm.

Moreover, the thickness "s" of the plate at said notch 8 is variable in a range between 1.3 and 1.7 mm, also in this case with a machining tolerance of at least 5%.

In a preferred embodiment, such thickness "s" is chosen equal to 1.5 mm when the thickness of the plate 2 is equal to 2.1 mm.

A use of the internal bone plate fixation device of the present invention is now described.

Once a relatively non-invasive incision is made in the skin and the flesh of the patient subject of implantation, it is possible to position the bone plate over the physis in such a way that the two lobed portions 23 and 24 are respectively in contact with the epiphysis and metaphysis of the bone to be treated.

A retaining wire inserted into the cartilage of the physis passing into through hole 9 in the central portion of joining of the plate 2, allows fixing of the plate 2 in its position, even if only temporarily.

Fixing screws 5 are initially inserted in the holes 3, 4 in such a way as to penetrate into the corresponding epiphyseal and metaphyseal portions of the bone until the head 10 reaches and is placed in contact with the cup-like shaped seat 12 and the axis Y of the cup-like shaped section 12 coincides with the axis of fixing screw 5.

The greater thickness "s" of the plate 2 allows to initially accommodate the head of screws 5, almost including them, in the respective housing seats 12.

During the growth of the physial tissue, fixing screws 5 are subjected to a dragging action which determines an angular spreading in the course of the entire treatment, i.e. a rotation of fixing screws 5 over a plane longitudinal to the bone plate 2, distancing from the joining portion 15.

The presence of groove 14 ensures achievement of an end contact between the stem of fixing screws 5 and the lower edge of holes 3, 4, distancing from the joining portion 15, i.e. at extremities 20 or 21 respectively.

In this way it is provided and determined an angular spread of fixing screws 5 that is greater than the one which would occur in the absence of groove 14, allowing the whole fixation device 1, i.e. bone plate 2 and fastening screws 5, to follow the bone growth for the entire duration of the treatment.

The greater thickness "s" of the bone plate of the present invention makes it possible to house and conceal with greater ease the head 10 of fixing screws 5 with respect to all known solutions, even when the screws have undergone their maximum angular excursion due to the growth of the physial tissue.

Advantageously, the bone plate described above has a flat conformation of uniform thickness with absence of protuberances, such as to avoid chafing regions with soft tissue surrounding the site of implantation.

Yet advantageously, the aforementioned conformation of the bone plate does not require complex and expensive manufacturing methods.

Furthermore, it is observed that use of a rigid material constituting the bone plate according to the invention, determines a greater resistance for the device to the stresses than for devices using flexible constituting material.

The bone plate according to the invention solves the technical problem and achieves numerous advantages, including that of preventing the breakage of the fixing screws, ensuring the complete correction of bone deformation by means of a single surgery.

The presence of the groove allows preventing the fixing screws from reaching an anticipated end position, thus avoiding repositioning of the screws before the end of the treatment.

The invention claimed is:

1. Internal bone plate fixation device for use as a means of synthesis in anatomical regions with poor coating of soft tissues, of the type comprising a bone plate that is bilobate or having eight-like shape comprising a pair of portions adapted to be respectively associated to an epiphysis and to a metaphysis of a bone and joined by a restricted central portion and in each of which is formed at least one through hole for receiving a corresponding screw for fixing to the bone, wherein the bone plate is flat with substantially constant thickness and is delimited by opposite surfaces, parallel with a single recess or notch transversal to a longitudinal axis of the bone plate, formed on only one of said opposite surfaces for housing a growth cartilage of the bone; the thickness of the bone plate being less than an eighth of its maximum longitudinal extension.

2. Fixation device according to claim 1, wherein said thickness is selected in a range between 1.5 and 2.3 mm.

3. Fixation device according to claim 2, wherein said thickness is chosen equal to 2.1 mm.

4. Fixation device according to claim 1, wherein said notch is arched and formed in said restricted central portion, and wherein a thickness at said notch of the bone plate is selected in a range between 1.3 and 1.7 mm.

5. Fixation device according to claim 4, wherein said thickness at said notch is chosen equal to 1.5 mm.

6. Fixation device according to claim 1, wherein the bone plate is bilobate and substantially shaped as an eight.

7. Fixation device according to claim 1, characterised in by comprising at least a third hole passing through said bone plate in the restricted central portion of joining to receive a guiding cable for temporary fixing of the bone plate.

8. Fixation device according to claim 1, wherein each of said holes comprises a circular mouth on a surface opposite to said notch, the circular mouth providing access to a seat with cup-like or hemispherical shape for a tilting housing of a head of a corresponding fixing screw.

9. Fixation device according to claim 8, wherein a cylindrical hole is opened onto a bottom of said cup-like shaped seat and is designed to accommodate a stem of the fixing screw; at least one groove tapered in the cup-like shaped seat and in the cylindrical hole being provided on a bottom portion of the cup-like shaped seat toward an extremity of the bone plate.

10. Fixation device according to claim 9, wherein said groove is a cylindrical or conical hole having an axis which is tilted with respect to an axis of said cylindrical hole.

11. Fixation device according to claim 8, wherein said substantially hemispherical seat receives a corresponding head of a fixing screw, either along the axis of the through hole or tilted by a predetermined angle with respect to said axis of the through hole.

12. Fixation device according to claim 8, wherein when the screw is inserted with its axis tilted with respect to the axis of the hole, at least an upper edge of head of the screw is housed completely in the substantially hemispherical seat under the circular edge.

13. Fixation device according to claim 1, wherein said bone plate has rounded upper and lower peripheral edges.

14. Fixation device according to claim 1, wherein the dimensions have a machining tolerance of at least 5%.

\* \* \* \* \*